United States Patent [19]

Chu et al.

[11] Patent Number: 4,493,614
[45] Date of Patent: Jan. 15, 1985

[54] PUMP FOR A PORTABLE VENTILATOR

[75] Inventors: Raymond D. Chu, Boulder; Marc A. Bergman, Lafayette, both of Colo.

[73] Assignee: Lifecare Services, Inc., Boulder, Colo.

[21] Appl. No.: 534,988

[22] Filed: Sep. 27, 1983

Related U.S. Application Data

[63] Continuation-in-part of Ser. No. 433,450, Oct. 8, 1982, abandoned.

[51] Int. Cl.³ .................. F04B 49/06; F04B 35/04; A61M 16/00
[52] U.S. Cl. .................... 417/22; 417/415; 128/204.21; 128/205.18; 74/57; 92/33
[58] Field of Search ............... 417/410, 415, 418, 22; 74/57, 58; 92/31, 33; 128/204.21, 205.18, 205.14, 205.15

[56] References Cited

U.S. PATENT DOCUMENTS

| | | | |
|---|---|---|---|
| 862,867 | 8/1907 | Eggleston | 417/390 |
| 1,580,131 | 4/1926 | Ghiardi | 92/33 |
| 2,061,869 | 11/1936 | Gilbert et al. | 417/418 |
| 2,389,918 | 11/1945 | Macgill | 74/58 X |
| 2,462,571 | 2/1949 | Thompson et al. | 91/275 X |
| 3,010,887 | 11/1961 | Baumgarten et al. | 74/18.2 X |
| 3,208,388 | 9/1965 | Glasgow | 417/415 X |
| 3,461,866 | 8/1969 | Ritchie | 92/240 X |
| 4,004,299 | 1/1977 | Runge | 3/1.7 |
| 4,076,021 | 2/1978 | Thompson | 128/205.18 |
| 4,145,166 | 3/1979 | Justice | 74/58 X |
| 4,175,475 | 11/1979 | Eckhardt | 92/33 |
| 4,180,375 | 12/1979 | Magnussen, Jr. | 417/22 |
| 4,221,543 | 9/1980 | Cosentino et al. | 417/22 |
| 4,243,029 | 1/1981 | Apple | 128/205.18 X |
| 4,262,667 | 4/1981 | Grant | 128/204.21 |
| 4,276,003 | 6/1981 | Perkins et al. | 417/415 |

FOREIGN PATENT DOCUMENTS

| | | | |
|---|---|---|---|
| 2822030 | 12/1978 | Fed. Rep. of Germany | 128/205.18 |
| 1541852 | 3/1979 | United Kingdom | 128/204.21 |

Primary Examiner—William L. Freeh
Assistant Examiner—Paul F. Neils
Attorney, Agent, or Firm—Burton & Dorr

[57] ABSTRACT

A pump primarily intended for use in a portable ventilator. The pump includes a piston-cylinder arrangement in which the piston is reciprocally moved within the cylinder by rotating a shaft. The shaft is threaded and mounted for rotation within the cylinder at a fixed location along the axis of the cylinder. The piston has an aperture through its center and the shaft extends substantially between the end walls of the cylinder and through the center of the piston. The piston is held against rotation relative to the shaft and cylinder by a collapsible hinge and is attached to the shaft by an arrangement including a ball nut and sealing nut. The piston forms a variable volume, working chamber with one end of the cylinder and in operation, the shaft is selectively rotated to move the piston toward and away from the end wall. This positioning of the shaft within the cylinder reduces the overall size of the pump and specifically adapts it for use in a portable ventilator in which size limitations are critical.

24 Claims, 5 Drawing Figures

PUMP FOR A PORTABLE VENTILATOR

FIELD OF THE INVENTION

This invention relates to the field of ventilators and more particularly to the field of pumps for portable ventilators.

BACKGROUND OF THE INVENTION AND PRIOR ART

Ventilators are commonly used to supply air or air enriched with oxygen to the lungs of a person having difficulty breathing on his own. Typically, such individuals either cannot breathe by themselves or are only able to breathe insufficient amounts of air on their own Still others can breathe normally some of the time but irregularly and insufficiently at other times. Consequently, ventilators are used in some cases constantly by the individual whereas in other cases, they are utilized only occasionally as for example while sleeping if there is a significant possibility the individual may lapse into a state where he fails to breathe involuntarily.

Virtually all ventilators include pumps that are capable of delivering a selected volume of air under a selected pressure for a selected time duration and at selected time intervals to a person. Ideally, a ventilator's operating parameters may be very sensitively adjusted to fulfill the unique respiratory needs of a particular person. In some instances, a ventilator may be utilized to wean a person from reliance on artificial respiration to a state where he independently and reliably respirates. In such a mode of operation, the ventilator supplies pressurized air to the person at infrequent time intervals to encourage the person to independently respirate but will provide sufficient artificial respiration to the person in the event he fails to do so. A ventilator in this mode of operation preferably includes means for sensing the independent respiration of the person and for actuating an alarm signal if the independent respiration falls below a selected frequency.

Most ventilators heretofore utilized have included an electric motor operatively connected through a complex crank arm assembly to a piston contained within a cylinder In the operation of such ventilators, air is drawn into the cylinder through an inlet port as the piston is moved in one direction within the cylinder whereupon the movement of the piston is then reversed to compress the air and force it through an outlet port in the cylinder to the patient. The crank arm assemblies utilized in such ventilators are relatively complex primarily because of the need to vary the stroke length of the piston so that a selected, variable quantity of air may be supplied to the patient. Moreover, such crank arm assemblies tend to be relatively bulky and noisy in operation which are highly undesirable traits in a portable ventilator where space is at a premium and quietness of operation is greatly preferred.

The present invention dispenses with a crank arm assembly and replaces it with a threaded, rotatable shaft. The shaft is driven by a motor and the piston moves within the cylinder in response to the rotation of the threaded shaft. The ventilator of the present invention is relatively simple and compact in construction and quiet in operation.

A patentability search was conducted for the present invention and the following patents were developed:

| U.S. Pat. No. | Inventor | Issue Date |
|---|---|---|
| 3,208,388 | Glasgow | September 28, 1965 |
| 3,225,758 | Morch | December 28, 1965 |
| 3,651,804 | Spiller | March 28, 1972 |
| 3,658,443 | Fumagalli | April 25, 1972 |
| 4,014,415 | Pickel | March 29, 1977 |
| 4,022,076 | Metz | May 10, 1977 |
| 4,145,165 | Perkins et al. | March 20, 1979 |
| 4,155,356 | Venegas | May 22, 1979 |
| 4,262,667 | Grant | April 21, 1981 |
| 4,276,003 | Perkins et al. | June 30, 1981 |

Of these patents, the Glasgow patent is believed to be the most relevant as it discloses a piston-cylinder type of pump in which the piston is reciprocated by a ball nut mounted on a threaded shaft. However, as best seen in Glasglow's FIGS. 2 and 5, his threaded shaft is positioned externally of his cylinder adding size to his pump in contrast to the present invention in which the shaft is positioned within the cylinder and passes through an aperature in the piston itself.

The inventors are also aware of a device manufactured by North American Phillips Company for transforming rotational motion into translational motion. The device includes an electric motor provided with a longitudinally hollowed armature. A ball bearing nut is mounted on the armature and operatively contacts a threaded shaft extending through the armature. Operation of the electric motor causes a rotation of the armature and ball bearing nut, which causes a concurrent translation of the threaded shaft.

SUMMARY OF THE INVENTION

The present invention involves a pump for a portable ventilator. The pump includes a cylinder having at least one end wall and fluid inlet and outlet ports. A piston is mounted within the cylinder for reciprocal movement along the axis of the cylinder toward and away from the end wall. The piston has a first side extending about the axis with an external diameter substantially equal to the internal diameter of the cylinder. The piston has a second side spaced from the first side and an aperature extending through the piston between its sides. The aperature extends about the axis and the pump further includes a threaded shaft rotatably mounted within the cylinder and extending substantially for the length of the entire cylinder. The shaft is mounted at a fixed location along the axis of the cylinder and additionally extends through the aperature in the piston. The piston is held against rotation relative to the shaft and cylinder by a collapsible hinge and is attached to the shaft by an arrangement including a ball nut and sealing nut. The piston forms a variable volume, working chamber with the end wall of the cylinder and in operation, the shaft is selectively rotated to move the piston toward and away from the end wall.

The pump also includes a transformer for transferring line voltage of about 120 volts down to 12 to 13 volts on which the pump motor is then operated. In this manner, the electric motor of the pump is not directly connected to the primary electric circuit of 120 volts adding to the overall safety of the device. Further, the step down voltage allows the pump to alternately be operated by an internal or external battery. Sensors for detecting and controlling the operation of the pump and in particular the reciprocal movement of the piston are also disclosed as are alternate ways to seal the piston to the shaft to prevent any flow of air through the piston's aperature from one side of the piston to the other during operation of the pump With the design of the present invention, a relatively compact and quiet pump is provided which is particularly adapted for use in a portable ventilator.

DETAILED DESCRIPTION OF THE PREFERRED EMBODIMENTS

Figure 1:
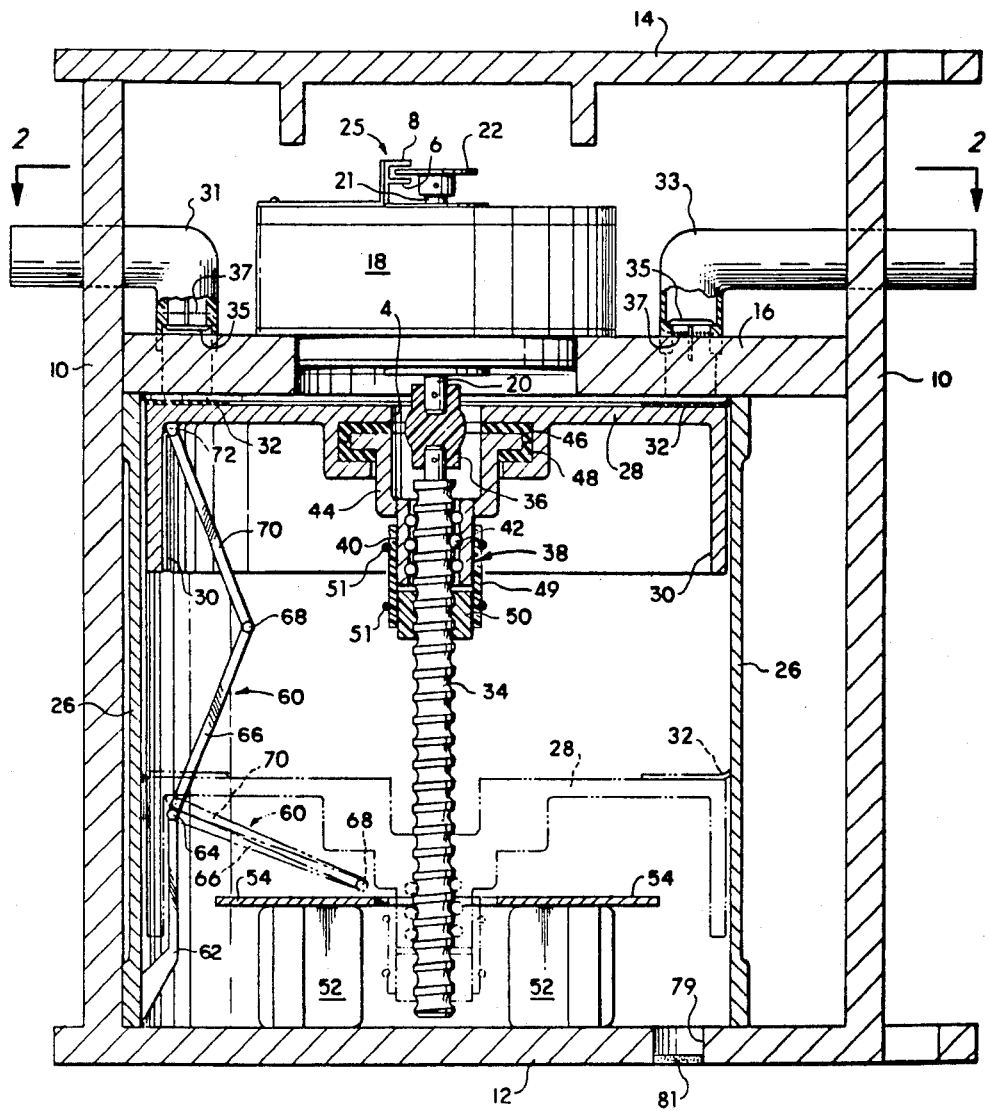
FIG. 1 is a partial cross-sectional view of a portable ventilator in accordance with one embodiment of the present invention.
Figure 2:
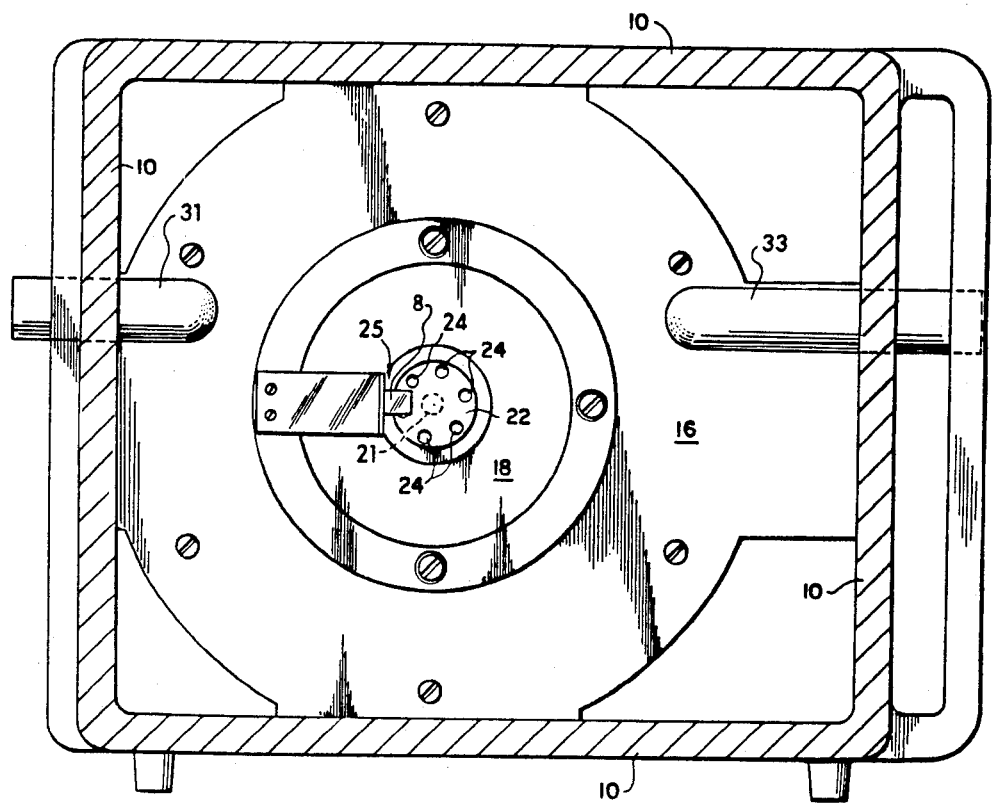
FIG. 2 is a top view of the portable ventilator depicted in FIG. 1 taken along line 2—2 of FIG. 1.

Referring now to the drawings wherein like reference numerals and symbols refer to the same item, there is shown in FIGS. 1 and 2 a portable ventilator according to one embodiment of the present invention. The ventilator includes a generally rectangular shaped housing having four side walls 10 and end plates 12 and 14. A generally circular mounting plate 16 extends laterally across the housing interior and is fixedly secured within the housing to the side walls 10.

An electric motor 18 having a selected power rating is mounted on the outer surface of the mounting plate 16 between the end plates 12 and 14. The electric motor 18 includes an armature, one end 20 of which extends through the mounting plate 16. Fixedly mounted on the other armature end 21 is a disc 22 which rotates concurrently with the armature. The disc 22 is provided with a series of aperatures 24 (see FIG. 2) located at equiangular positions near the disc's periphery. Mounted on the motor 18 housing is a rotation sensing device 25. The rotation sensing or detecting device 25 has two portions 6 and 8 which essentially straddle the periphery of the disc 22 (see FIG. 1). One of the portions (e.g., the lower one 6) is an energy source and produces, for example, a beam of light directed upwardly toward the disc 22 near its periphery. The other portion 8 of the rotation sensing or detecting device 25 has an energy receiving member (e.g., light sensitive transistor) therein detecting the passage of the light beam through an aperture 24. Operation of the electric motor 18 causes the armature to rotate producing a concurrent rotation of the disc 22. As the disc 22 rotates, light passes through the aperatures 24 and is detected by portion 8 of the device 25. This information is then utilized to determine the speed of angular rotation and the amount of angular rotation of the armature which directly correlates to position and movement of the piston 28.

Disposed between the mounting plate 16 and the end plate 12 is a cylinder 26. As shown in FIG. 1, the plates 12 and 16 act as end walls for the cylinder 26. Enclosed within the cylinder 26 is a disc shaped piston 28, the external diameter of which approximately equals the internal diameter of the cylinder 26. The piston 28 is adapted for longitudinal translation and reciprocation within the cylinder 26. To help guide the piston 28 during its translation and reciprocation within the cylinder 26, a cylindrical skirt 30 is preferably mounted about the periphery of the piston 28 and extends along and closely adjacent to the cylinder 26. The skirt 30 ensures that the piston 28 does not tilt significantly out of a plane perpendicular to the axis of the cylinder 26. Preferably the cylinder 26, piston 28, and skirt 30 are formed of a fiber glass epoxy with a TEFLON lining for relatively low friction, low wear contacts. A sealing ring 32 is preferably mounted about the periphery of the piston 28 on the side of the piston 28 opposite to the skirt 30. The outermost edge of the ring 32 is warped slightly upwardly and is of such a diameter that the outer edge of the ring contacts the cylinder 26. The ring 32 is preferably formed of a low friction material composed of TEFLON (ninety percent) and graphite (ten percent) and the outer edge of the ring 32 is preferably slightly flexible.

The mounting plate 16 is provided with an inlet port 31 and an outlet port 33 for permitting air to enter into and the pressurized air to exit from, respectively, the cylinder chamber. The ports 31 and 33 are provided with suitable one way valves such as leaf valves 35 held in place by air screens 37. The motor 18 is mounted to the plate 16 to form an air tight seal therewith and the end of the armature at 20 extends through the plate 16 where it is connected to a threaded shaft 34 by means of a resilient, flexible coupling 36. In this manner, the rotation of the armature at 21 causes a concurrent rotation of the threaded shaft 34. The coupling 36 and the threaded shaft 34 are aligned with the axis of the cylinder 26.

As best seen in FIG. 1, the piston 28 has a central aperature 4 extending from one side to the other through which the coupling 36 and shaft 34 are received as the piston 28 moves within the cylinder 26 from the position shown in solid lines to the one shown in dotted lines. A ball nut 38 is mounted on the threaded shaft 34. The ball nut 38 comprises a metal sleeve or cylinder 40 having confined ball bearings 42 protruding from its interior surface. The ball bearings 42 are adapted to ride in a known manner in the grooves of the threaded surface of the shaft 34. The ball nut 38 is threadably coupled to a bell shaped bracket 44 which in turn is fixedly attached to the piston 28. The flared ends of the bracket 44 are clamped between rubber rings 46 and 48 to the piston 28. The rubber rings 46 and 48 provide a dual function of providing an air tight seal between the bracket 44 and the piston 28 and as well as providing a relatively quiet movement of the piston 28. Rotation of the threaded shaft 34 causes the ball nut to translate along the shaft 34, which in turn causes a corresponding translation of the piston 28 within the cylinder 26 between the extreme positions as shown in solid and dotted lines in FIG. 1 or any other positions depending upon how the motor 18 is set to operate.

The interior surface of the ball nut 38 is slightly spaced from the surface of the threaded shaft 34. Because of this spacing, fluid may flow from one side of the piston 28 through the space between the threaded shaft 34 and the metal sleeve 40 of the ball nut 38 to the other side of the piston 28. Such air flow or seepage usually is significant enough to render the compression effect of the piston 28 ineffective. To prevent the air flow or seepage, a sealing nut 50 is mounted on the threaded shaft 34 adjacent the ball nut 38. The nut 50 is preferably formed of low friction plastic and as "Turcite" which is sold by Ball Screws & Actuators Company, Inc. located at 3520 Victor St., Santa Clara, Calif. 95050. The nut 50 is provided with a threaded interior surface corresponding virtually identically with the threaded surface of the shaft 34. In this manner, air flow between the nut 50 and the threaded shaft 34 is substantially prevented. The nut 50 may be sealed in an abutting relationship with the ball nut 38 by means of an adhesive. However, it is preferred that the external diameters of the metal sleeve 40 of the ball nut 38 and the nut 50 are equal and that a connecting sleeve 49 having an internal diameter equal thereto is joined to them and frictionally held in place by bands 51. In this way, an air tight seal between the ball nut 38 and the nut 50 is formed and ball nut 38 and the nut 50 are confined to move integrally as a unit along the threaded shaft 34.

In an alternate embodiment of the present invention, the ball nut 38 may be eliminated and the nut 50 threadably secured directly to the bracket 44. Since the ball nut 38 produces some noise during its translation along the threaded shaft 34 and the nut 50 produces virtually no noise, this embodiment of the invention would be even quieter in operation.

To insure that the proper power is supplied to the electric motor 18, a transformer 52 may be inserted between the primary source of electric energy for powering the ventilator (e.g., conventional 120 volt alternating current source) and the electric motor 18. In a preferred embodiment of the present invention, the transformer 52 has a toroid shape and is positioned to surround the lower end of the threaded shaft 34 adding to the compactness of the pump. The transformer 52 is preferably mounted on the end plate 12 with an abutment plate 54 mounted on its upper surface.

Figure 5:
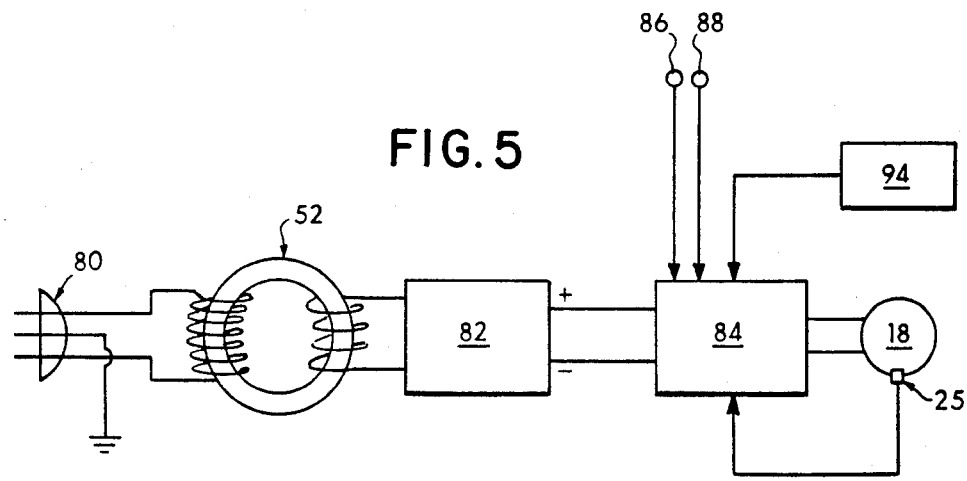
FIG. 5 is a schematic diagram of the preferred circuitry for controlling the operation of the pump of the present invention.

In operation, electric energy from a primary electric circuit 80 (see FIG. 5) which for example could be a conventional 120 volt alternating current source is stepped down to 12 to 13 volts at transformer 52 and transferred to a secondary circuit by magnetic induction. The motor 18 is preferably run off the secondary circuit with includes rectifier 82 and microprocessor 84. Microprocessor 84 operates motor 18 controlling, for example, its direction, speed, and amount of rotation in accordance with the input control settings (e.g., length of desired stroke, speed including desired acceleration and deceleration) at 86 and 88 and the feed back from rotation sensor 25. As the piston 28 descends in FIG. 1 from the position shown in solid lines, air is drawn through inlet port 31 into the working chamber between the piston 28 and end wall 16. As piston 28 continues to descend, the air below it is forced for example out port 79 and air filter 81 in the end wall 12. In operation, the ventilator is preferably supported as shown in FIG. 2 wherein end wall 12 is then positioned vertically. When the piston 28 reaches the position shown in dotted lines in FIG. 1 (or any other pre-set position), rotation of the motor 18 and shaft 34 is halted and subsequently reversed wherein the piston 28 moves toward the end wall 16 compressing the air in the working chamber and forcing the air through outlet port 33 to the patient.

The rotation of the threaded shaft 34 causes a corresponding translation and reciprocation of the piston 28. Thus, the piston 28 can translate in a variety of manners to produce a variety of pulses of air for a person in need of artificial respiration. The regulation of the power to the electric motor 18 produces a corresponding regulation of the volume of air in each pulse, the duration and curve of each pulse, the air pressure in each pulse, and the duration of the interval between air pulses.

Because the sensing device 25 correlates armature rotation with piston translation, it is important that the piston 28 and the ball nut 38 not rotate with respect to the cylinder 26 since such rotation would not be detected and therefore would introduce an error into the determined length of piston translation. Also, such rotation would promote increased wear along the radially outer edge of the ring 32. To prevent such rotation, the ventilator of the present invention is provided with a hinge assembly 60. The hinge assembly 60 includes an upstanding first arm 62 fixedly mounted on the lowermost portion of the interior surface of the cylinder 26. The first arm 62 is bent slightly radially inwardly so that the piston skirt 30 does not contact the arm 62 when the piston 28 is at its lowest point of translation within the cylinder 26. The upper end of the first arm 62 is provided with a first knuckle 64 and is located at a point slightly below the piston 28 at its lowest point of translation. The first knuckle 64 is mounted also at the lower end of a second arm 66 which in turn is interconnected through a second knuckle 68 to a third arm 70. The upper end of the third knuckle 70 is provided with a third knuckle 72 connected to the piston 28. As shown in FIG. 1, the hinge assembly 60 extends (solid lines) and collapses (dotted lines) as the piston 28 translates to prevent rotation of the piston 28 and the attaching arrangement including ball nut 38, sealing nut 50, sleeve 49, and bracket 44 relative to the shaft 34 and cylinder 26.

Preferably, the ventilator electric motor 18 may be selectively adapted to be powered by an external AC source, an external DC source or an internal, rechargeable DC source (such as a storage battery). Also preferably, the ventilator includes means for sensing the insufficiency of a power source and for automatically switching to a different power source.

Figure 3:
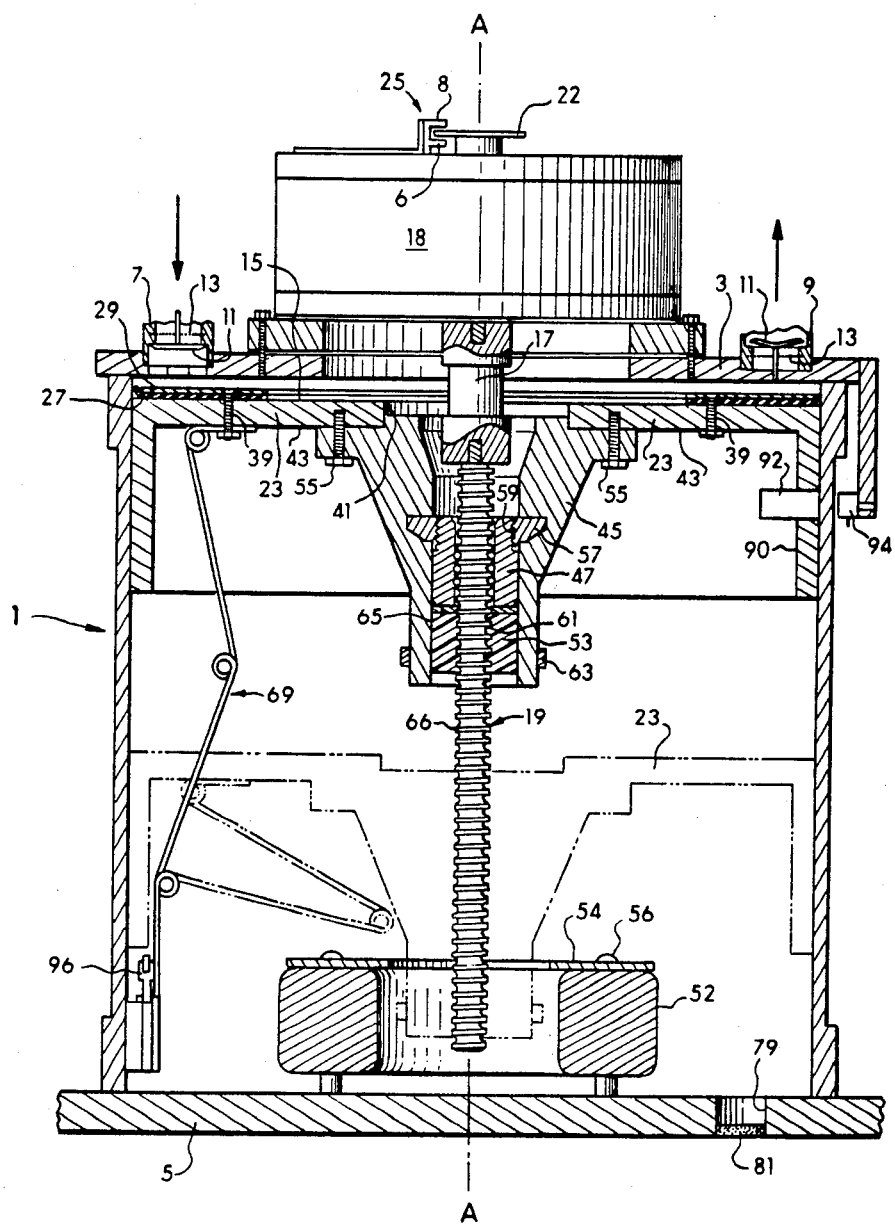
FIG. 3 is a view similar to FIG. 1 showing the preferred embodiment of the present invention.

In a manner similar to the embodiment of FIGS. 1 and 2, the preferred embodiment of FIG. 3 has a cylindrical member 1 extending along an axis A—A between end walls 3 and 5. End wall 3 has inlet and outlet ports 7 and 9 passing through it which perferably have one way valves such as leaf valves 11 supported therein as for example by air screens 13. The variable speed, reversible motor 18 is sealingly mounted on the outside of the end wall 3. Coupling 17 connects the threaded shaft 19 to the motor 18 for rotation about the longitudinal axis of the shaft 19. The shaft 19 is preferably mounted with its longitudinal axis substantially coincident with axis A—A of the cylindrical member 1.

As in the embodiments of FIGS. 1 and 2, the piston member 23 is mounted within the cylindrical member 1 for reciprocal movement along the axis A—A toward and away from the end wall 3. The piston member 23 has a first side 15 extending about the axis A—A. The first side 15 has an external diameter substantially equal to the internal diameter of the cylindrical member 1. Seal member 27 is mounted to the first side 15 by plate 29 and screws 39 to enhance the sealing engagement of the piston member 23 and the cylindrical member 1. The piston member 23 has a central aperature 41 extending symmetrically about axis A—A and extending between sides 15 and 43 of the piston member 23. Piston member 23 is attached to the shaft 19 by the arrangement including block 45, ball nut 47, and sealing nut 53.

More specifically, the block 45 is secured to the side 43 of the piston member 23 by screws 55. Metal insert 57 is molded into the plastic block 45 and ball nut 47 is secured thereto as for example by mating screw threads 59. Sealing nut 53 has a threaded interior surface at 61 conforming substantially to the threaded exterior surface of the shaft 19 and forms a substantially fluid-tight seal therewith. Band 63 about the block 45 serves to compress the block 45 about the sealing nut 53 and frictionally hold the sealing nut 53 against relative rotation. Preferably, a Teflon washer 65 soaked with a lubricant is positioned between the ball nut 47 and the sealing nut 53 to lubricate and clean the threads 66 of the shaft 19 as the pump operates.

Ball nut 47 and sealing nut 53 together with coupling 17 mount the shaft 19 for rotation around the axis A—A. At least a portion and preferably the entire shaft 19 extends longitudinally within the cylindrical member 1 between its end walls 3 and 5 for economy of space. The coupling 17 further serves to maintain the shaft 19 at a fixed location along the axis A—A with the shaft 19 within the cylindrical member 1 and extending through the aperature 41 in the piston member 23. As in the embodiment of FIGS. 1 and 2, collapsible hinge 69 in the manner of hinge 60 in FIG. 1 prevents the piston member 23 from rotating about the axis A—A relative to the cylindrical member 1.

In operation of the preferred embodiment of FIG. 3, the motor 18 is rotated in a first direction to rotate the shaft 19 attached thereto by coupling 17. With collapsible hinge 69 preventing rotation of the piston member 23 and the attaching arrangement of block 45, ball nut 47 and sealing nut 53, the piston member 23 and attaching arrangement are moved downwardly in FIG. 3 along and relative to the rotating shaft 19. This movement draws fluid (e.g., air) through the leaf valve 11 in the inlet port 7 into the working chamber formed between side 15 of the piston member 23 and the end wall 3 of the cylindrical member 1. This working chamber is a variable volume one and as the piston member 23 continues to descend in FIG. 3 to the position shown in dotted lines, air continues to be drawn into it through inlet port 7. At the position shown in dotted lines in FIG. 3 (or any other predetermined position as set by the operator), the rotational direction of the motor 18 and shaft 19 is reversed whereupon the piston member 23 ascends in FIG. 3 pumping the air through leaf valve 11 in outlet port 9. In the preferred embodiment of FIG. 3, the piston skirt 90 has a magnet 92 mounted therein with a magnetic detector 94 positioned at a fixed location outside the cylindrical member 1. The detector 94 senses the passage of the magnet 92 and feeds this information to the microprocessor 84 (see FIG. 5). The microprocessor 84 in turn uses this information to confirm and reference the location of the piston member 28. For example, the detector 94 can be positioned at the end of the piston's stroke. In this way, the microprocessor 84 will know when the piston member 28 has reached this reference point when the ventilator is first started up (e.g., the ventilator may have been previously turned off with the piston member 28 other than at the end of its stroke). Also, the microprocessor 84 can confirm and make adjustments for each cycle by using the input from detector 94 as a zero reference point. The preferred embodiment additionally includes limit switch 96 (see FIG. 3) to automatically reverse the drive of motor 18 if the piston member 28 accidentally exceeds its preferred limit and engages the safety switch 96. The transformer 52 of the embodiment of FIG. 3 is also preferably mounted about the shaft 19 for economy of space and is secured along with abutment plate 54 to end wall 5 by screws 56.

Figure 4:
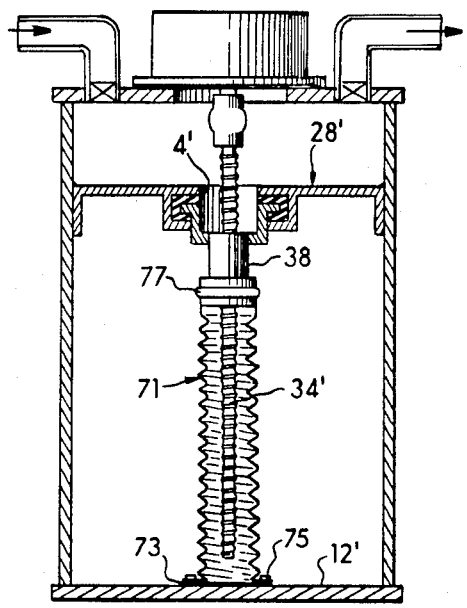
FIG. 4 is a partial cross-sectional view illustrating another embodiment of the present invention in which a bellows is sealingly mounted within the pump to prevent the passage of air through the central aperature of the piston from one side of the piston to the other.

FIG. 4 illustrates an additional embodiment in which the sealing mechanism to prevent air flow through the aperature 4' of the piston member 28' includes a bellow 71. As shown, the bellows 71 is sealingly mounted about the shaft 34' between the end wall 12' and piston member 28'. More specifically, the bellows 71 is secured at one end by annular gasket 73 and screws 75 to the end wall 12' with the other end being sealingly mounted by band 77 about the ball nut 38.

While several embodiments have been shown and described in detail, it is to be understood that various modifications and changes may be made to them without departing from the scope of the invention.

We claim:
1. A pump comprising:
a cylinder capable of containing a fluid and having at least one end wall, said cylinder having fluid inlet and outlet ports;
a piston disposed substantially within said cylinder for substantially, longitudinally reciprocating within said cylinder, the external diameter of said piston being substantially equal to the internal diameter of said cylinder, and said piston provided with an aperture substantially, longitudinally therethrough;
a rotatable shaft extending substantially longitudinally through said cylinder and through the aperture in said piston;
means disposed substantially within said cylinder for reciprocating said piston within said cylinder in response to the rotation of said shaft, said means including means for substantially preventing the rotation of said piston during its reciprocation within said cylinder wherein said rotation preventing means includes a collapsible hinge, and,
means for substantially preventing the flow of any fluid with in said cylinder from one longitudinal side of said piston to the other longitudinal side of said piston when said piston reciprocates within said cylinder.

2. A pump comprising:
a cylinder capable of containing a fluid and having at least one end wall, said cylinder having fluid inlet and outlet ports;
a piston disposed substantially within said cylinder for substantially, longitudinally reciprocating within said cylinder, the external diameter of said piston being substantially equal to the internal diameter of said cylinder, and said piston provided with an aperture substantially, longitudinally therethrough;
a rotatable shaft extending substantially longitudinally through said cylinder and through the aperture in said piston;
means disposed substantially within said cylinder for reciprocating said piston within said cylinder in response to the rotation of said shaft;
means for substantially preventing the flow of any fluid within said cylinder from one longitudinal side of said piston when said piston reciprocates within said cylinder; and,
said pump further includes an electric motor for selectively rotating said shaft, a primary electric circuit, a secondary electric circuit operatively connected to said electric motor, and a transformer for transferring energy from said primary circuit to said secondary circuit by magnetic induction, said transformer disposed adjacent to an end wall of said cylinder wherein said transformer is fashioned substantially in the shape of a toroid and wherein siad transformer substantially surrounds said shaft.

3. A pump according to claim 2 wherein said flow preventing means includes a bellows surrounding said shaft and having one end thereof sealingly connected to an end wall of said cylinder and the other end thereof sealingly connected to said piston.

4. A pump according to claim 2 wherein said rotatable shaft is provided with a threaded exterior surface and wherein said reciprocating means includes a nut mounted on said shaft such that the nut translates along said shaft in response to the rotation of said shaft, the nut having a threaded interior surface conforming substantially identically with the shaft threaded surface such that fluid flow along said shaft, between the nut and said shaft, is substantially prevented.

5. A pump according to claim 2 further comprising means for substantially preventing the rotation of said piston during its reciprocation within said cylinder.

6. A pump according to claim 2 wherein said rotatable shaft is provided with a threaded exterior surface and wherein said reciprocating means includes a ball nut coupled to said piston and mounted on said shaft such that the ball nut translates along said shaft in response to the rotation of said shaft.

7. A pump according to claim 6 wherein said flow preventing means includes a nut mounted on said shaft and having a threaded interior surface conforming substantially identically with the shaft threaded surface such that fluid flow along said shaft, between the nut and said shaft, is substantially prevented.

8. A pump according to claim 6 wherein said flow preventing means includes a bellows surrounding said shaft and having one end thereof sealingly connected to an end wall of said cylinder and the other end thereof sealingly connected to the ball nut.

9. A pump comprising:
a cylinder capable of containing a fluid and having at least one end wall, said cylinder having fluid inlet and outlet ports;
a piston disposed substantially within said cylinder for substantially, longitudinally reciprocating within said cylinder, the external diameter of said piston being substantially equal to the internal diameter of said cylinder, and said pion provided with an aperture substantially, longitudinally therethrough;
a rotatable shaft extending substantially longitudinally through said cylinder and through the aperture in said piston, said rotatable shaft being provided with a threaded exterior surface;
means disposed substantially within said cylinder for reciprocating said piston within said cylinder in response to the rotation of said shaft, said reciprocating means including a ball nut coupled to said piston and mounted on said shaft such that the ball nut translates along said shaft in response to the rotation of said shaft; and
means for substantially preventing the flow of any fluid within said cylinder from one longitudinal side of said piston to the other longitudinal side of said piston when said piston reciprocates within said cylinder, said flow preventing means including a second nut mounted on said shaft and having a threaded interior surface conforming substantially identically with the shaft threaded surface such that fluid flow along said shaft, between the second nut and said shaft, is substantially prevented and means for mounting said second nut to said ball nut wherein the second nut correspondingly translates integrally with the ball nut as a unit along said shaft in response to the rotation of said shaft.

10. The pump of claim 9 wherein said ball nut and said second nut have substantially cylindrical, external surfaces with respective first and second diameters and said means for mounting said second nut to said ball nut includes a member with a substantially cylindrical, inner surface having a third diameter, said first, second, and third diameters being substantially equal wherein portions of said ball nut and second nut are received within said member with the inner surface of said member respectively engaging the external surfaces of said ball nut and second nut.

11. A pump primarily intended for use in a ventilator, said pump comprising:
a substantially cylindrical member extending along an axis and having at least one end wall, said cylindrical member having fluid inlet and outlet ports,
a piston member and means for reciprocally moving said piston member along said axis toward and away from said end wall, said piston member having a first side extending about said axis with an external diameter substantially equal to the internal diameter of the cylindrical member, said piston member further having a second side spaced from the first side along said axis and an aperture extending through said piston member between said first and second sides,
said moving means including a shaft, means for rotatably mounting said shaft with at least a portion thereof at a fixed location along said axis, said portion extending substantially longitudinally within said cylindrical member and extending through the aperture of said piston member, means for rotating said shaft, and means attached between said piston member and said shaft portion for moving said piston member relative to and along said shaft portion within said cylindrical member in response to rotation of said shaft, said moving means further including means for preventing rotation of said piston member about said axis, said rotation preventing means including a collapsible hinge, and
means for substantially preventing any flow of fluid within said cylindrical member through said aperture between the first and second sides of said piston member as said piston member is moved within the cylindrical member whereby said cylindrical member and piston member form a variable volume, working chamber between the first side of the piston member and the end wall of the cylindrical member wherein fluid enters and exits said working chamber through said ports in response to the reciprocal movement of said piston member within said cylindrical member.

12. A pump primarily intended for use in a ventilator, said pump comprising:
a substantially cylindrical member extending along an axis and having at least one end wall, said cylindrical member having fluid inlet and outlet ports,
a piston member and means for reciprocally moving said piston member along said axis toward and away from said end wall, said piston member having a first side extending about said axis with an external diameter substantially equal to the internal diameter of the cylindrical member, said piston member further having a second side spaced from the first side along said axis and an aperture extending through said piston member between said first and second sides, said moving means including a shaft, means for rotatably mounting said shaft with at least a portion thereof at a fixed location along said axis, said portion extending substantially longitudinally within said cylindrical member and extending through the aperture of said piston member, means for rotating said shaft, and means attached between said piston member and said shaft portion for moving said piston member relative to and along said shaft portion within said cylindrical member in response to rotation of said shaft, said means for rotating said shaft including an electric motor, said electric motor having a power source comprising a primary electric circuit, a secondary electric circuit directly connected to said motor, and a transformer whereby electrical power from said primary circuit is transferred to said secondary circuit by magnetic induction so that said electric motor is not directly connected to said primary electric circuit and wherein said transformer is substantially toroid-shaped and said pump includes means for mounting said transformer substantially about said shaft, and means for substantially preventing any flow of fluid within said cylindrical member through said aperture between the first and second sides of said piston member as said piston member is moved within the cylindrical member whereby said cylindrical member and piston member form a variable volume, working chamber between the first side of the piston member and the end wall of the cylindrical member wherein fluid enters and exits said working chamber through said ports in response to the reciprocal movement of said piston member within said cylindrical member.

13. The pump of claim 12 wherein said cylindrical member has a second end wall spaced from the first mentioned end wall along said axis and said flow preventing means includes a bellows and means for sealingly mounting said bellows about said shaft between said second end wall and said piston member.

14. The pump of claim 12 wherein said means for reciprocally moving said piston member within said cylindrical member along said axis includes means for preventing rotation of said piston member about said axis.

15. The pump of claim 12 wherein said piston member further includes a magnetic member fixed thereto and movable therewith and said pump further includes means for detecting passage of said magnetic member by a fixed location along the axis of said cylindrical member.

16. The pump of claim 12 wherein said primary electric circuit has a voltage of about 120 volts and said secondary circuit has a voltage of about 12 volts.

17. The pump of claim 12 wherein said cylindrical member has a second end wall spaced from the first mentioned end wall along said axis and said transformer mounting means includes means for mounting said transformer substantially about said portion of said shaft within said cylindrical member between the end walls thereof.

18. The pump of claim 12 further including means for detecting the rotation of said shaft, said detecting means including a disc, means for mounting said disc for rotation with said shaft, said disc having a plurality of aperatures therethrough and said detecting means including an energy source on one side of said disc and an energy receiving member on the other side whereby energy from said source passes through said aperatures and is received by said receiving member as said disc rotates.

19. The pump of claim 12 wherein the aperature through said piston member extends substantially symmetrically about said axis, said shaft has a longitudinal axis and said means for rotatably mounting said shaft includes means for mounting the shaft with the longitudinal axis thereof substantially coincident with the axis of said cylindrical member.

20. The pump of claim 12 wherein said cylindrical member extends along said axis for a first distance and said shaft portion at said fixed location extends longitudinally within said cylindrical member along the axis thereof substantially for said first distance.

21. The pump of claim 12 wherein said shaft portion has a threaded exterior surface and said means attached between said piston member and said shaft portion includes a nut and means for mounting said nut on said shaft portion whereby said nut and piston member move relative to and along said shaft portion within said cylindrical member in response to rotation of said shaft.

22. The pump of claim 21 wherein said nut is a ball nut and said flow preventing means includes a second nut having a threaded interior surface conforming substantially to the threaded exterior surface of said shaft portion and forming a substantially fluid-tight seal therewith.

23. A pump primarily intended for use in a ventilator, said pump comprising:

a substantially cylindrical member extending along an axis and having at least one end wall, said cylindrical member having fluid inlet and outlet ports, a piston member and means for reciprocally moving said piston member along said axis toward and away from said end wall, said piston member having a first side extending about said axis with an external diameter substantially equal to the internal diameter of the cylindrical member, said piston member further having a second side spaced from the first side along said axis and an aperature extending through said piston member between said first and second sides, said moving means including a shaft, means for rotatably mounting said shaft with at least a portion thereof at a fixed location along said axis, said portion extending substantially longitudinally within said cylindrical member and extending through the aperature of said piston member, means for rotating said shaft, and means attached between said piston member and said shaft portion for moving said piston member relative to and along said shaft portion within said cylindrical member in response to rotation of said shaft, said shaft portion having a threaded exterior surface and said means attached between said piston member and said shaft portion including a ball nut and means for mounting said ball nut on said shaft portion whereby said ball nut and piston member move relative to and along said shaft portion within said cylindrical member in response to rotation of said shaft, and means for substantially preventing any flow of fluid within said cylindrical member through said aperature between the first and second sides of said piston member as said piston member is moved within the cylindrical member whereby said cylindrical member and piston member form a variable volume, working chamber between the first side of the piston member and the end wall of the cylindrical member wherein fluid enters and exits said working chamber through said ports in response to the reciprocal movement of said piston member within said cylindrical member and wherein said flow preventing means includes a second nut having a threaded interior surface conforming substantially to the threaded exterior surface of said shaft portion and forming a substantially fluid-tight seal therewith, and means for mounting said second nut to said ball nut for movement integrally therewith as a unit in response to rotation of said shaft.

24. The pump of claim 23 wherein said ball nut and said second nut have substantially cylindrical, external surfaces with respective first and second diameters and said means for mounting said second nut to said ball nut includes a member with a substantially cylindrical, inner surface having a third diameter, said first, second, and third diameters being substantially equal wherein portions of said ball nut and second nut are received within said member with the inner surface of said member respectively engaging the external surfaces of said ball nut and second nut.

* * * * *